United States Patent
Mückner et al.

(10) Patent No.: US 6,389,205 B1
(45) Date of Patent: May 14, 2002

(54) BRIGHTNESS-CONTROLLED ENDOSCOPE ILLUMINATION SYSTEM

(75) Inventors: Andreas Mückner, Berlin; Jens Peter Wulfsberg, Neritz, both of (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 4 days.

(21) Appl. No.: 09/679,256

(22) Filed: Oct. 4, 2000

(30) Foreign Application Priority Data

Oct. 5, 1999 (DE) .......................................... 199 47 812

(51) Int. Cl.⁷ ................................................ G02B 6/06
(52) U.S. Cl. ........................................ 385/117; 362/574
(58) Field of Search ................................ 385/117, 118, 385/116; 362/572, 574, 552, 295

(56) References Cited

U.S. PATENT DOCUMENTS

| | | | | |
|---|---|---|---|---|
| 3,698,099 A | * | 10/1972 | Matsura | 351/205 |
| 3,730,632 A | * | 5/1973 | Chikama | 356/3 |
| 3,843,865 A | * | 10/1974 | Nath | 219/121.6 |
| 4,356,534 A | * | 10/1982 | Hattori | 362/276 |
| 4,402,311 A | * | 9/1983 | Hattori | 600/117 |
| 4,404,496 A | * | 9/1983 | Hosoda | 315/151 |
| 4,415,952 A | * | 11/1983 | Hattori et al. | 348/68 |
| 5,016,975 A | * | 5/1991 | Sasaki et al. | 362/279 |
| 5,115,126 A | | 5/1992 | Ams et al. | |
| 5,989,181 A | | 11/1999 | Dutting et al. | |

FOREIGN PATENT DOCUMENTS

| | | |
|---|---|---|
| DE | 19508100 | 8/1996 |
| WO | 98/08430 | 8/1997 |

* cited by examiner

Primary Examiner—Brian Sircus
Assistant Examiner—Hae Moon Hyeon
(74) Attorney, Agent, or Firm—Rankin, Hill, Porter & Clark LLP

(57) ABSTRACT

An illumination system for endoscopes having a light source of which the brightness is controlled by a control unit. A hook-up cable containing a bundle of optic fibers is provided to transmit the light from the light source to a light guide situated in the endoscope and extending to a distal end of the endoscope. At least one fiber of the bundle of fibers is optically coupled at one end near the light source with a light sensor. The light sensor cooperates with the control unit to control the brightness of the light source.

4 Claims, 1 Drawing Sheet

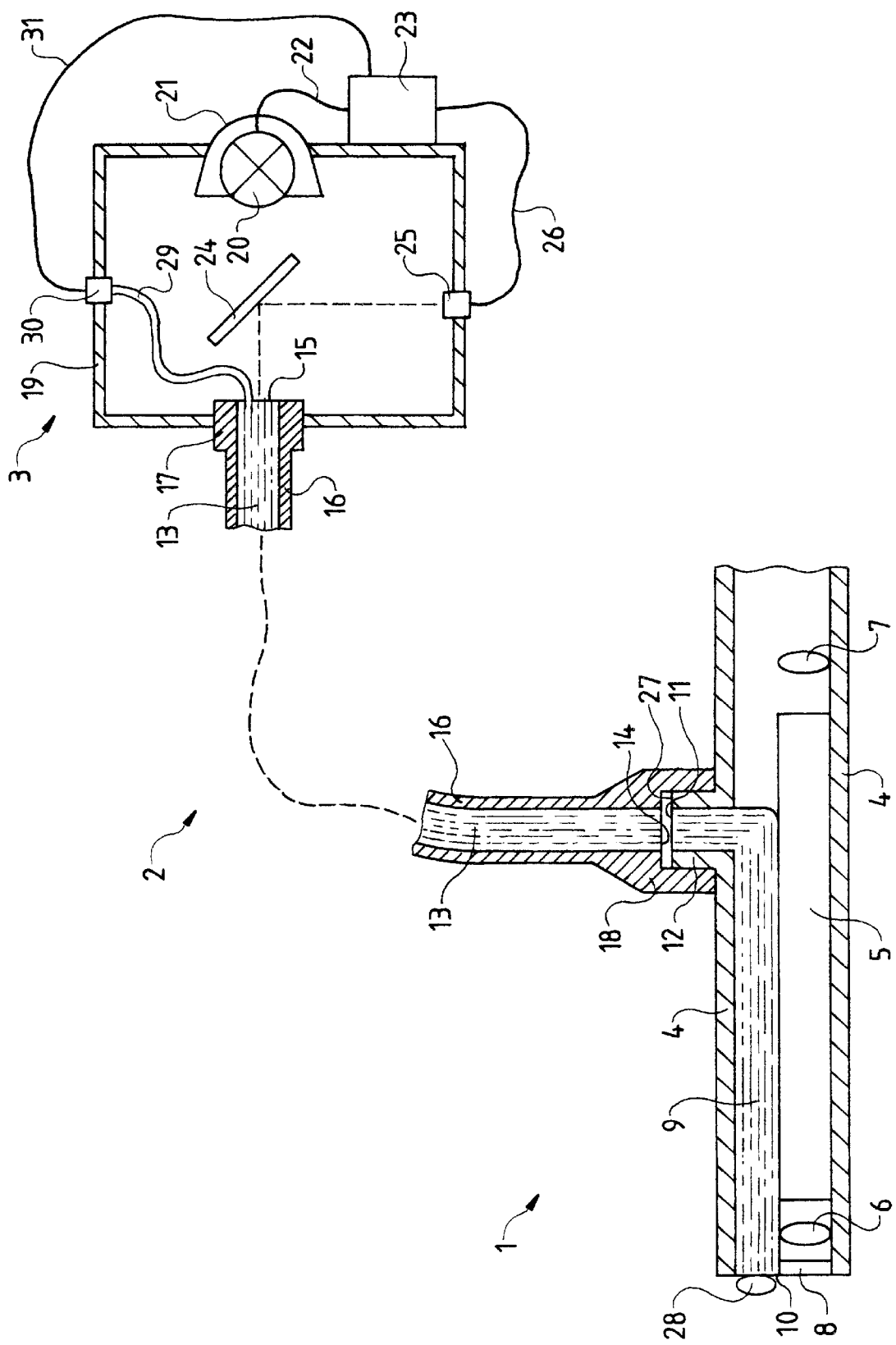

BRIGHTNESS-CONTROLLED ENDOSCOPE ILLUMINATION SYSTEM

BACKGROUND OF THE INVENTION

1. Field of the Invention

The present invention relates to an illumination system for an endoscope including a light source whose brightness is controlled by a control unit and wherein a hook-up cable containing a bundle of optic fibers is provided to transmit light from the light source to a light guide installed in the endoscope and running as far as a distal end of the endoscope.

2. Description of Related Art

Most endoscope applications are in a dark environment, such as the human bladder, and require an illuminating device for diagnostic viewing. As regards the present-day conventional illuminating devices, the light source is very powerful and mounted outside the endoscope. The light source supplies the light to the endoscope through a hook-up cable. Light is supplied to a fiber optics bundle that transmits the light to a light guide installed inside the endoscope. Light is emitted from a distal end of the light guide and illuminates the viewing field adjacent the endoscope distal end.

The cross-sections available in an endoscope are very limited. Accordingly, comparatively thin light guides or fiber optics are used. Since these thin light guides or fiber optics must transmit extremely high light intensities, a number of problems are created.

When endoscopes are interchanged, for instance endoscopes of different length or viewing directions, the hook-up cable typically will be disconnected from an endoscope hookup stub. If, when changing endoscopes, the cable is temporarily laid aside with the light source ON, then the light beam issuing from the end of the hook-up cable, due to its high intensity, may cause damage or even ignite an irradiated material such as a cover cloth.

Moreover, the distal end of the endoscope hook-up cable may be damaged if, with the light source ON, a reflecting or absorbing obstacle is situated directly in front of the end of the fiber optics or light guide. Illustratively absorbent soiling, such as blood in the case of a medical endoscope, may reach the free distal ends of the fiber optics of the hook-up cable or light guide. In this situation, on account of light absorption, strong heating and destruction may ensue.

The patent document WO 98/08430 discloses a light-guide hook-up cable with an integrated electric line and with a sensor situated at its coupling end facing the endoscope. The sensor, in the disconnected state, transmits through the lines a signal to the light source control unit to lower the light intensity of the light source. This feature prevents high-intensity light from issuing from the disconnected end of the hook-up cable. This design, however, incurs the drawback that the remaining problems cited above remain unsolved and creates additional technical problems by requiring additional conductors in the hook-up cable.

SUMMARY OF THE INVENTION

The present invention is directed toward a simple and economical solution to the aforementioned problems in the art. The present invention is further directed toward a conventional illumination system that is adapted for the case of a disconnected hook-up cable and also adapted to accommodate the situation wherein the hook-up cable or the light guide on the endoscope side is soiled.

In accordance with the present invention, a light sensor is present at the light-source side end of the fiber optics and looks at at least one fiber. Accordingly, the sensor sees or receives light that is issued by the light source, passes through the fiber optics, and is reflected back at the fiber optics-side end.

If the hook-up cable end is disconnected from the endoscope, the light radiates or projects freely into the ambient as far as distant objects and the fibers reflect only a little of the light. If the hook-up cable is connected to the endoscope, then light will be reflected in the zone of the hook-up fitting and there results a higher, back-reflected light level that can be detected by the sensor. In this manner, the control unit is able to sense and determine whether the hook-up cable is appropriately connected to the endoscope. In the case of a disconnected endoscope, the control unit is able to lower the light source intensity or shut it off in order to minimize damage from emitted light.

Even when the terminal surface of the fiber optics near the endoscope is soiled, the sensor will detect a different back-reflection and will be able to reduce or shut off the light source to prevent destroying the hook-up cable by overheating. If the hook-up cable is connected to the endoscope or, in the case of a bundle of optic fibers, passing through the hook-up cable and installed in the endoscope, the sensor is advantageously used to sense soiling, for instance blood drops, at the distal end of the endoscope or on the end surface of the light guide, in order to minimize the light intensity and to prevent damage or destruction caused thereby.

A single fiber will suffice, in principle, for the purposes of the invention. However, several fibers or even the full bundle of optic fibers may be used for viewing.

The light can be transmitted using a single fiber, several fibers or even the full bundle of optic fibers at the end surface of the bundle near the light sensor. For instance, a light-transmitting corner reflector may be used for transmitting light from the light source to the bundle of fibers. In this procedure, however, the light sensor may be subjected to spurious light from the light source.

In further accordance with the present invention, the fiber or bundle of fibers can be directly coupled to the light sensor while averting spurious light interference. The fiber or fiber bundle used for the back reflection may be integrated into the bundle of fibers of the hook-up cable. Advantageously, however, the fiber or small fiber bundle used for back reflection can be laterally added in a simple manner to the fiber bundle of the hook-up cable after its manufacture. In this manner the end of the fiber or fiber bundle near the light source will exit in a simple manner toward the light sensor. Because the distal fiber end is situated at the edge of the fiber bundle, the edge of the connection site of the hook-up cable and endoscope is especially easily observed and, as a result, reflections at the connection site are easily noted.

The light sensor may be designed to discriminate only with respect to the intensity of the back-reflected light or, also, to sense color. In this manner and, for instance, in the event of blood-drop soiling, the light sensor is able to detect this condition by means of the color and in this dangerous situation it is able to initiate, for instance, an emergency program. Color recognition moreover may be used very advantageously to recognize endoscopes bearing different color codes. Such color codes may be provided in the form of rings of different colors disposed at the hook-up fitting for the hook-up cable. Therefore, the light-source control unit may recognize which particular endoscope is connected. Such recognition may be useful, for instance, for the purpose of correspondingly adjusting the light intensity, to use given filters and the like.

BRIEF DESCRIPTION OF THE DRAWING

These and further features of the present invention will be apparent with reference to the following detailed description and drawing, the drawing showing a cross-section of an endoscope with hook-up cable and light source according to the present invention.

DETAILED DESCRIPTION OF THE PREFERRED EMBODIMENTS

The drawing shows an endoscope 1, a hook-up cable 2 and a light source 3.

The endoscope 1 comprises a tubular stem 4 of which the distal stem portion in some of its cross-section receives an image transmitting system 5. The image transmitting system 5 may be, for instance, in the form of a bar lens optics or a bundle of optic fibers. An objective lens 6 is indicated distally from the image transmitting system 5. Proximally relative to the image transmitting system 5 there is an intermediate lens element 7 illustratively optically coupled to an ocular (not shown), a video camera or the like. Illustratively, the image transmitting system 5 also can be replaced by a video camera mounted to the objective lens 6. A window 8 is mounted distally from the objective lens 6 and seals the optic system from ambient effects.

The remaining cross-section of the distal zone of the tubular stem 4 is filled by a light guide 9 in the form of a bundle of optic fibers. The light guide 9 runs from a distal end surface 10, into which terminate the optic fibers, to a proximal end surface 11 in a connection stub 12 substantially orthogonal to the tube stem 4.

The hookup cable 2 is conventionally flexible and receives a bundle of optic fibers 13 comprising a distal end surface 14 and a proximal end surface 15. The bundle of optic fibers 13 is enclosed in a sheath 16 fitted with a connecting flange 17 at the proximal end near the light source 3 and with a socket 18 at the distal end near the endoscope. The socket 18 affixes the hook-up cable 2 in the shown assembly to the connection stub 12 of the endoscope 1. In this configuration the end surfaces 11 of the light guide 9 in the endoscope 1 and the end surfaces 14 of the bundle of optic fibers 13 at the distal end of the hook-up cable 2 are opposite and flush for optimal light transmission.

The light source 3 comprises a housing 19. The proximal end of the hook-up cable 2 near the light source 3 is affixed to the housing 19 via the cable connection flange 17. This affixation site also can be designed to be disengageable in a known manner. The proximal end surface 15 of the bundle of optic fibers 13 is opposite an electric bulb 20 with reflector 21 in order to be illuminated in an appropriately focused manner by the bulb.

In this highly schematic illustrative embodiment, the light source 20 can be controlled by means of its power supply 22 connected to a control unit 23. In an omitted variation, the control unit 23 also may control, for instance, an optical stop or shutter between the bulb 20 and the proximal end surface 15 of the bundle of optic fibers 13 to be illuminated.

This design shall determine light that will control the brightness of the bulb 20 and issues from the distal end surface 14 of the bundle of optic fibers 13 or from the distal end surface 10 of the light guide 9 and reflected again into the light transmitting system. The drawing shows two illustrative embodiments in this regard.

In the first embodiment, a light-transmitting mirror 24 is mounted between the bulb 20 and the proximal end surface 15 of the bundle of optic fibers 13 at an angle of 45°. The mirror 24 transmits light issuing from the bulb 20 to the proximal end surface 15 but reflects light issuing from the proximal end surface 15 laterally onto a light sensor 25. The sensor 25 is connected through a control conductor 26 to the control unit 23.

If, as shown, the hook-up cable 2 is appropriately affixed to the stub 12 of the endoscope 1, then light issuing from the bundle of optic fibers 13 in the boundary zone of the coupling site will be reflected from the rim of the connection stub 12, in particular from the annular surface 27 at the end face which includes the light guide 9. The reflected light will run in the opposite direction through the bundle of optic fibers 13 and, by means of the mirror 24, to the light sensor 25.

When the hook-up cable 2 is removed from the endoscope 1, the reflection at hook-up cable distal end surface 14 will be altered. Less light will be reflected. The light sensor 25 and the control unit 23 will detect this change and may initiate appropriate actions. Particularly, the control unit 23 may reduce or shut off the light output from the bulb 20. As a result, if the distal end of the hook-up cable 2 were laid on a cover cloth, any lightly flammable materials therein will not be illuminated at high intensity and therefore will not be charred or ignited.

The light sensor 25 furthermore can recognize other changes in reflection. For instance, when a blood drop 28 is deposited on the distal end surface 10 of the light guide 9 at the endoscope side. Blood is extremely opaque to light and absorbs any light issuing from the end surface 10. Because of the very high light intensity, the distal end 10 then is quickly and strongly heated. Such heating may destroy the light guide 9 and the structure in the vicinity of the end of the light guide 9, for instance the window 8. To prevent such an occurrence, the light sensor 25 is able to detect the change in this shown situation and power to the bulb 20 can be reduced or shut off.

In the event of inappropriate handling, for instance during difficult surgery, a blood drop also may reach the distal end surface 14 of the bundle of optic fibers 13. In this case the control unit 23 in corresponding manner assures power reduction or shut-off of the bulb 20.

In the second shown embodiment, the mirror 24 and the light sensor 25 have been eliminated. One fiber 29, or a bundle of several fibers of the bundle 13 extend proximally beyond the end surface 15 as far as a light sensor 30 to which the fiber(s) is (are) coupled directly. In this manner spurious light interference from the intense light of the bulb 20 are averted.

In the manner already discussed in relation to the light sensor 25, the light sensor 30 is connected by a conductor 31 to the control unit 23.

The fiber or the bundle of fibers connected to the light sensor terminate(s) in the distal end surface 14 of the bundle of optic fibers 13 where they are able to monitor the reflection conditions. Just as in the first embodiment described above, it is possible in this second embodiment to monitor the connection of the hook-up cable 2 to the endoscope 1 and to detect interfering soiling on the end surfaces, for instance by the shown blood drop 28.

The proximally extended fiber 29 or a correspondingly small bundle of fibers, following manufacture of the bundle of optic fibers 13, can be arranged near the edge of the bundle of optic fibers 13. As a result the fiber 29 is situated at the rim in the distal end surface 14 of the bundle of optic fibers 13, and the fiber 29 then will be especially sensitive to changes in reflections when hooking up the endoscope.

The light sensors 25 or 30 may be color sensitive so that, depending on the incident light color, they will transmit through the conductors 26 and 31 different control signals to the control unit 23. If the annular surfaces 27 at the connection stub 12 of the endoscope 1 are of different colors corresponding to the particular type of endoscope, then the light sensors 25 or 30 are able to sense different, hooked-up endoscopes. Consequently, the control unit 23, depending on the particular connected endoscope, is able to automatically adjust the bulb 20 to the light intensity required by the particular endoscope. Where needed, and depending on the type of endoscope, illustratively different filters may be inserted between the bulb 20 and the end surface 15.

What is claimed is:

1. An illumination system for an endoscope (1) that is fitted with a light source (3), a brightness of said light source is controlled by a control unit (23), a hook-up cable (2) containing a bundle of optic fibers is provided to transmit the light from the light source (3) to a light guide (9) installed in then endoscope (1) and running to a distal end (10) of the endoscope, wherein at least one fiber (20) of the bundle of fibers (13) is optically coupled at end near the light source (20) with a light sensor (25, 30), said light sensor being operable, in cooperation with the control unit (23), to control the brightness of the light source.

2. The illumination system as claimed in claim 1, wherein said at least one fiber (29), at the end of the bundle of fibers (13) situated near the light source, extends beyond said bundle as far as the light sensor (30).

3. The illumination system as claimed in claim 1, wherein said at least one fiber (29) at an end (14) of the bundle of fibers (13) near the endoscope terminates adjacent the rim of said bundle of fibers.

4. The illumination system as claimed in claim 1, where in the light sensor (25, 30) is designed to emit different signals depending on a color of the incident light.

* * * * *

UNITED STATES PATENT AND TRADEMARK OFFICE
CERTIFICATE OF CORRECTION

PATENT NO. : 6,389,205 B1
DATED : May 14, 2002
INVENTOR(S) : Muckner et al.

It is certified that error appears in the above-identified patent and that said Letters Patent is hereby corrected as shown below:

<u>Column 6,</u>
Line 1, delete "then" and insert -- the --.
Line 2, delete "(20)" and insert -- (29) --.
Line 13, delete "the" (second occurrance) and insert -- a --.
Line 15, delete "where" and insert -- wherein --.
Line 16, delete "in"

Signed and Sealed this

Twenty-second Day of October, 2002

Attest:

JAMES E. ROGAN
Attesting Officer     Director of the United States Patent and Trademark Office